United States Patent
Mase et al.

(10) Patent No.: US 7,314,727 B2
(45) Date of Patent: Jan. 1, 2008

(54) METHODS TO FACILITATE DIAGNOSIS OF NORMAL PRESSURE HYDROCEPHALUS

(75) Inventors: Mitsuhito Mase, Aichi (JP); Hiroya Nakau, Osaka (JP); Takashi Inui, Hyogo (JP); Naomi Eguchi, Osaka (JP); Yoshihiro Urade, Kyoto (JP); Kosuke Seiki, Ibaraki (JP); Hiroshi Oda, Ibaraki (JP); Hiroshi Nakajima, Ibaraki (JP); Nobuyuki Sato, Ibaraki (JP)

(73) Assignees: Maruha Corporation, Tokyo (JP); Japan Science and Technology Corporation, Saitama (JP); Osaka Bioscience Institute, Osaka (JP)

( * ) Notice: Subject to any disclaimer, the term of this patent is extended or adjusted under 35 U.S.C. 154(b) by 448 days.

(21) Appl. No.: 10/333,336

(22) PCT Filed: Jun. 7, 2001

(86) PCT No.: PCT/JP01/04811

§ 371 (c)(1),
(2), (4) Date: Jan. 21, 2003

(87) PCT Pub. No.: WO02/08756

PCT Pub. Date: Jan. 31, 2002

(65) Prior Publication Data

US 2003/0190678 A1 Oct. 9, 2003

(30) Foreign Application Priority Data

Jul. 21, 2000 (JP) ............................ 2000-221248

(51) Int. Cl.
G01N 33/53 (2006.01)
G01N 33/537 (2006.01)
G01N 33/543 (2006.01)
G01N 33/573 (2006.01)
G01N 33/542 (2006.01)

(52) U.S. Cl. .................. 435/7.92; 435/7.1; 435/7.4; 435/7.72; 435/7.9; 435/7.94

(58) Field of Classification Search ................. None
See application file for complete search history.

(56) References Cited

FOREIGN PATENT DOCUMENTS

WO    WO 99/64621 A    12/1999

OTHER PUBLICATIONS

DSM-IV, American Psychiatric Association, Fourth Edition, 1994, pp. 133, 138-139.*
Clinical Chemistry, 1996, 42, 12, pp. 1984-1991.*
J. Chromatogr. A, 1998, 802, 143-8.*
J. Chromatogr. B, 1997, 687, pp. 141-147.*
Hiraoka et al., Journal of Analytical Bio-Science, Mar. 31, 2000, vol. 23, No. 2, pp. 110-116.
Urade et al., The Journal of Biological Chemistry, Nov. 5, 1987, vol. 262, No. 31, pp. 15132-15136.
Tachibana et al., Proc. Natl. Acad. Sci., USA, Nov. 1987, vol. 84, pp. 7677-7680.
Home page of the 11th Symposium on Intracranial Pressure and Brain Monitoring (ICP 2000), Abstract Book, Abstract No. O4-4, Jun. 2000.
H. Oda et al., Proc. Japan Acad, 72 Ser. B, pp. 108-111, 1996.
L. Symon et al., J. Neurosurg., vol. 42, pp. 258-273, 1975.
M. Mase et al., Curr. Tr. Hyd. (Tokyo), vol. 8, pp. 13-18, 1998.
M. Tullberg et al., Neurology, vol. 60, pp. 1122-1127, 1998.
A. Hoffmann et al., J. Neurochem., vol. 61, pp. 451-456, 1993.
M. Zahn et al., Neursci. Let., vol. 154, pp. 93-95, 1993.
K. Watanabe et al., Biochem. Biophys. Res. Commun., vol. 203, No. 2, pp. 1110-1116, 1994.

* cited by examiner

*Primary Examiner*—Olga N. Chernyshev
(74) *Attorney, Agent, or Firm*—Birch, Stewart, Kolasch & Birch, LLP

(57) ABSTRACT

The present invention relates to methods for differentiating demential diseases comprising measuring the concentration of human lipocalin-type prostaglandin D synthase in a sample of a body fluid collected from a subject and kits for differentiating demential diseases comprising an antibody specific to human lipocalin-type prostaglandin D synthase.

4 Claims, 4 Drawing Sheets

METHODS TO FACILITATE DIAGNOSIS OF NORMAL PRESSURE HYDROCEPHALUS

This application is the national phase under 35 U.S.C. § 371 of PCT International Application No. PCT/JP01/04811 which has an International filing date of Jun. 7, 2001, which designated the United States of America.

TECHNICAL FIELD

The present invention relates to methods for differentiating demential diseases, more specifically methods for differentiating demential diseases comprising measuring a concentration of human lipocalin-type prostaglandin D synthase (hereinafter periodically referred to as "L-PGDS") in a sample of a body fluid collected from a subject and differentiation kits for use in the methods.

BACKGROUND ART

With the aging of society, there is an ongoing increase in the number of people suffering from demential diseases. Demential diseases can be induced by an enormous variety of etiologies. It is therefore very difficult to make an exact differential diagnosis of such a disease, and no therapy has been established for many demential diseases. Among demential diseases, normal pressure hydrocephalus (hereinafter referred to as NPH) including symptomatic normal pressure hydrocephalus following subarachnoid hemorrhage or cerebral meningitis and idiopathic normal pressure hydrocephalus of unknown cause is known to be dramatically improved by surgery (e.g. ventriculoperitoneal shunt). However, there can be little expectation that surgery will have any effect in improving symptoms of demential diseases found in elderly people, such as Alzheimer's disease, Parkinson's disease and cerebrovascular dementia, or the symptoms of diffuse brain injury, characterized by cerebral atrophy and ventricular enlargement. Thus, it is important to be able to differentiate at an early stage between NPH, which is treatable by surgery, and dementia for which surgical treatment is not effective. However, it is difficult to make such differentiation.

A classic diagnostic method for determing suitability for surgery involves continuously measuring a cerebrospinal pressure for a period of one day via drainage from lumbar vertebra to cerebrospinal cavity, to thereby monitor a pressure wave of cerebrospinal fluid (Symon, L., Dorsh, N. W. C., J. Neurosurg., 42: 258-273, 1975). However, this method is often clinically difficult because it requires a patient to be treated at rest in a bed in a clean environment, using appropriate instruments for continuous measurement and analysis and the like. Another method involves daily drainage of 40-50 ml of cerebrospinal fluid to assess improvements in symptoms, but this lacks reliability and carries a risk of complication such as infection of a site subjected to repeated puncture. A method for differentiating between atrophic Alzheimer-type senile dementia and NPH by assaying amyloid-related protein (α1-antichymotrypsin) in cerebral venous blood has been reported, but is not widely used because it requires invasive collection of cerebral venous blood and lacks effectiveness.

The rationale for monitoring a dynamic state of spinal fluid resides in the pathophysiology of these diseases. However, it is to be noted that measurement of a pressure wave of spinal fluid has been recently replaced by methods made possible by remarkable advances in diagnostic imaging. A conventional standard method involves RI or CT cisternography with a contrast medium injected into cerebrospinal cavity from lumbar vertebra to evaluate malabsorption of spinal fluid into circulation, but diagnosis resulting from use of this method has been reported not to always correlate properly to postoperative prognosis. A relatively new report proposes evaluating a flow of spinal fluid in the aqueduct of midbrain using MRI images (Mase, M. et al., Current Treatment for Hydrocephalus (Tokyo), 8:13-18, 1998). This is an attractive non-invasive method, but is still under development and remains ineffective for some cases. One of the reasons that this method has not come into widespread use is because it can be carried out in only limited facilities.

Among recent successful studies, a report proposes detecting NPH by assessing damage to nerve tissue based on neurofilament triplet protein (NFL) or glial fibrillary acidic protein (GFAP) in cerebrospinal fluid (Tullberg, M. et al., Neurology 60:1122-1127, 1998), but this method has not been made commercial yet.

As described above, surgery is effective for NPH, but there has not yet been developed any detection method for determining whether early surgical treatment of a patient suffering from a demential disease is required.

Prostaglandin D syntheses (PGDSs) include lipocalin type mainly localized in brain and hematopoietic organ type localized in spleen and mast cells, and the PGDS protein found in cerebrospinal fluid has been identified as lipocalin type. Lipocalin-type prostaglandin D synthase (L-PGDS) is an enzyme involved in biosynthesis of prostaglandin $D_2$ in the central nerve system (CNS) of various mammals. This enzyme is mainly produced in cerebral leptomeninges and arachnoid membrane and secreted into cerebrospinal fluid (hereinafter sometimes referred to as CSF). Recently, this L-PGDS has been shown to be identical with β-trace that was known to be present in abundance in CSF (Hoffmann A. et al., J. Neurochem., 61:451-456, 1993; Zahn M. et al., Neurosci. Let., 154:93-95, 1993; Watanabe, K. et al., Biochem. Biophys. Res. Commun., 203:1110-1116, 1994). Studies have been devoted to clinical uses of β-trace in various diseases of the central nerve system because it is a main member of human CSF proteins. However, the involvement or role of PGDS or L-PGDS in various demential diseases remains unexplaind.

An object of the present invention is therefor to provide a method capable of differentiating reliably and with a minimum of stress to a patient normal pressure hydrocephalus that was not detectable or difficult to reliably detect by various conventional test means. Another object of the present invention is to provide a kit for use in the differentiation method.

DISCLOSURE OF THE INVENTION

As a result of careful studies to attain the above objects, the inventors accomplished the present invention on the basis of the finding that demential diseases can be differentiated by using L-PGDS levels determined in a body fluid such as cerebrospinal fluid, blood or urine as an indicator.

Accordingly, the present invention provides a method for differentiating a demential disease comprising measuring a concentration of human lipocalin-type prostaglandin D synthase in a sample of a body fluid collected from a subject. The present invention also provides a kit for differentiating a demential disease comprising an antibody specific to human lipocalin-type prostaglandin D synthase.

THE MOST PREFERRED EMBODIMENTS OF THE INVENTION

Figure 1:
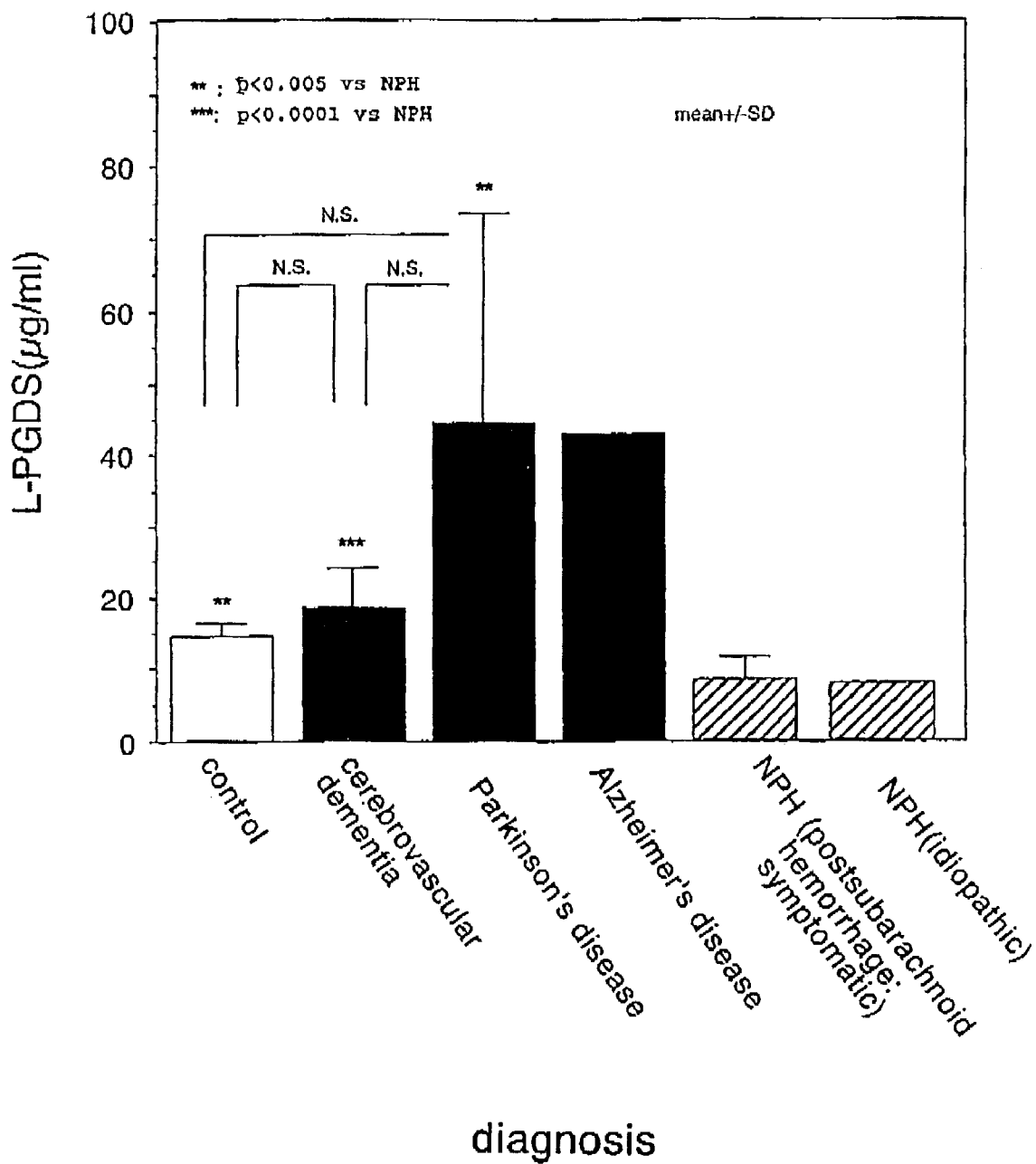
FIG. 1 shows assay results of L-PGDS levels in the cerebrospinal fluid of controls and patients with postsubarachnoid hemorrhage NPH and idiopathic NPH, cerebrovascular dementia, Parkinson's disease and Alzheimer's disease.

The sample assayed for L-PGDS in the present invention is a body fluid collected from a subject, specifically cerebrospinal fluid, blood or urine, etc. The method for determining L-PGDS levels in the sample is not specifically limited so far as it exactly reflects L-PGDS levels, such as immunoassays and enzymatic activity assays. However, immunoassays such as EIA, ELISA, RIA and FIA using a monoclonal or polyclonal antibody specific to L-PGDS are preferred from the viewpoint of the necessity of simultaneously assaying a large number of samples with convenience in the actual clinical field.

Among these immunoassays, especially preferred is sandwich ELISA using an L-PGDS-specific monoclonal antibody such as antibodies produced by hybridoma cell lines 1B7 (FERM BP-5709), 7F5 (FERM BP-5711). 6F5 (FERM BP-5710), 9A6 (FERM BP-5712) and 10A3 (FERN BP-5713). For determination by sandwich ELISA, an L-PGDS detection kit comprising the monoclonal antibody already established by the inventors can be used (WO97/16461). These cell lines have been internationally deposited under Budapest Treaty with the National Institute of Bioscience and Human-Technology of the Agency of Industrial Science and Technology (residing at 1-3, Higashi 1-Chome, Tsukuba-city, Ibaraki-prefecture, Japan).

In the present invention, NPH can be differentiated by using L-PGDS levels determined by the means described above as an indicator in comparison with L-GDS levels in controls or L-PGDS levels in patients with demential diseases other than NPH (e.g. Alzheimer's disease, Parkinson's disease, vascular dementia).

Demential diseases detected or differentiated by methods of the present invention include, for example, normal pressure hydrocephalus (NPH) including symptomatic normal pressure hydrocephalus following subarachnoid hemorrhage or cerebral meningitis and idiopathic normal pressure hydrocephalus of unknown cause. Methods of the present invention can be used to differentiate these NPHs from controls or other demential diseases such as vascular dementia, Alzheimer's disease or Parkinson's disease.

NPH such as symptomatic NPH and idiopathic NPH is characterized by significantly low L-PGDS levels in cerebrospinal fluid as compared with that of control subjects. NPH also shows significantly lower L-PGDS levels in cerebrospinal fluid as compared with other demential diseases such as vascular dementia, Alzheimer's disease and Parkinson's disease. No significant difference was found between controls and patients with vascular dementia or Parkinson's disease.

L-PGDS levels in CSF were determined in NPH patients divided into two groups, i.e. patients under 70 years of age (presenile NPH group) and at or more than 70 years of age (senile NPH group) to demonstrate that L-PGDS levels in the senile NPH group were higher than in the presenile NPH group but significantly lower than in control and dementia groups (demential diseases other than NPH including vascular dementia, Alzheimer's disease and Parkinson's disease), indicating that NPH can be differentiated. L-PGDS levels in cerebrospinal fluid from both presenile and senile NPH groups were significantly lower than both control and dementia groups (p<0.005).

The neuron specific enolase (NSE) and S-100 protein levels in CSF indicative of brain parenchymal damage were also determined by radioimmunoassay and immunoradiometric assay, respectively. The results showed that NSE levels in the CSF of each group increased in the order: presenile NPH group; senile NPH group; control group; and then dementia group. S-100 protein levels increased in the order: control group; dementia group; presenile NPH group; and then senile NPH group. NSE levels in cerebrospinal fluid showed no significant difference between groups except that presenile NPH group showed significantly lower levels than dementia group. S-100 protein levels in cerebrospinal fluid showed no significant difference between groups. Thus, L-PGDS was shown to be more useful for differentiating demential diseases than NSE and S-100 protein.

While the theory stated below remains speculative, the inventors infer that L-PGDS production in NPH may decrease for the following reasons. L-PGDS is produced in arachnoid cells and secreted into spinal fluid, but arachnoid cells undergo dysfunction or decrease in number by inflammatory changes of the arachnoid membrane at the acute stage in postsubarachnoid hemorrhage or postmeningitic NPH. This seems to result in decreased L-PGDS production as compared with controls. L-PGDS production does not seem to be decreased in other demential diseases as compared with NPH because dysfunction of the arachnoid membrane or circulatory failure of spinal fluid is not found in these diseases.

Methods of the present invention can be used to differentiate reliably and with a minimum of stress to a patient NPH that was not detectable or that was difficult to detect reliably using the various conventional test means available, thus allowing early determination of suitability of a patient for surgery. Differentiation can be more reliable by combining differentiation methods of the present invention with other diagnostic methods.

The present invention also provides a kit for differentiating a demential disease comprising an antibody specific to human lipocalin-type prostaglandin D synthase (L-PGDS). Suitable antibodies specific to L-PGDS include monoclonal or polyclonal antibodies specific to L-PGDS, preferably various L-PGDS-specific monoclonal antibodies mentioned above.

When an enzyme is used as a label for detection, the kit of the present invention can comprise the following component reagents:

(1) an enzyme-labelled monoclonal antibody, and (2) a substrate solution

A variant of said kit using sandwich ELISA can comprise the following reagents:

(1) a monoclonal antibody, (2) an enzyme-labelled monoclonal or polyclonal antibody, and (3) a substrate solution.

Another variant of said kit using biotin-avidin assay can comprise the following reagents:

(1) a biotinylated monoclonal antibody,
(2) an enzyme-labelled avidin or streptavidin, and
(3) a substrate solution.

Another variant of said kit using sandwich ELISA and biotin-avidin assay can comprise the following reagents:

(1) a monoclonal antibody,
(2) a biotinylated monoclonal or polyclonal antibody,
(3) an enzyme-labelled avidin or streptavidin, and
(4) a substrate solution.

For details of the process for preparing monoclonal and polyclonal antibodies used in the present invention see WO97/16461.

The following examples further illustrate the present invention without, however, limiting the scope of the invention thereto.

EXAMPLES

Reference Example

Determination of L-PGDS Levels

L-PGDS levels in body fluid samples were determined by sandwich ELISA.

(1) In order to prepare a standard curve, 300 μl/well of an anti-L-PGDS monoclonal antibody (clone: 7F5) capable of binding L-PGDS diluted to 4.4 μg/ml in 50 mM carbonate buffer (pH 9.6) was first added to a 96-well microtiter plate and immobilized by allowing the plate to stand overnight at 4° C. This plate was washed with phosphate-buffered physiological saline (pH 7.4, hereinafter referred to as PBS) three times, and then blocked by incubation with 300 μl/well of PBS containing 0.2% casein (pH 7.4, hereinafter referred to as blocking solution) at 30° C. for 90 minutes. Then, the blocked plate was washed with PBS containing 0.05% Tween 20 (T-PBS) three times and then incubated at 30° C. for 90 minutes with 100 μl/well of a standard L-PGDS solution (prepared by serial dilution of L-PGDS purified from CSF in blocking solution). After reaction, the plate was washed with T-PBS three times and incubated at 30° C. for 90 minutes with 100 μl/well of horseradish peroxidase-labelled anti-PGDS monoclonal antibody (clone: 1B7) diluted to 0.5 μg/ml in blocking solution. The plate was washed with T-PBS three times and then incubated at 30° C. for 30 minutes with 100 μl/well of a color developing solution (ABTS solution available from Boehringer-Mannheim), and then the reaction was stopped by adding 100 μl/well of a quenching solution (1.5% oxalic acid) and shaking on a plate mixer. The difference between the absorbances at 405 nm and 490 nm (A405 nm-A490 nm) was determined with a commercially available plate reader (Catalog # SK601 made by Seikagakusha) to prepare a standard curve.

The monoclonal antibodies used in the sandwich ELISA described above (clones: 1B7 and 7F5) were obtained by injecting 1.0 ml of pristane into the abdominal cavity of a mouse, implanting 1×10$^8$ cells of a cell line producing each antibody into the abdominal cavity of the mouse after 2 weeks, collecting the ascites after further 2 weeks and purifying the ascites by protein A affinity column chromatography (3-10 mg/ml). The cell lines producing the monoclonal antibodies described above are identified with the designations of the respective monoclonal antibodies and have been internationally deposited under Budapest Treaty with the National Institute of Bioscience and Human-Technology of the Agency of Industrial Science and Technology (residing at 1-3, Higashi 1-Chome, Tsukuba-city, Ibaraki-prefecture, Japan) under accession number FERM BP-5709 (originally deposited on Sep. 21, 1996) for 1B7 and accession number FERM BP-5711 (originally deposited on Jun. 6, 1996) for 7F5.

(2) L-PGDS levels in samples were determined by the sandwich ELISA described above after diluting the samples in blocking solution as appropriate.

Example 1

Determination of L-PGDS Levels in the Cerebrospinal Fluid of Control Subjects and Patients with Postsubarachnoid Hemorrhage NPH and Idiopathic NPH, Cerebrovascular Dementia, Parkinson's Disease and Alzheimer's Disease L-PGDS levels in the CSF collected from the lumbar vertebra of 6 controls with no abnormality except for intraorbital hematoma or headache, 12 cases of postsubarachnoid hemorrhage NPH, 1 case of idiopathic NPH, 3 cases of cerebrovascular dementia, 12 cases of, Parkinson's disease and 1 case of Alzheimer's disease were determined.

L-PGDS levels in the CSF of each group were 14.58±1.67 (μg/ml, mean±SD) in control group, 8.51±3.20 in postsubarachnoid hemorrhage NPH, 8.12 in idiopathic NPH, 26.45±5.67 in vascular dementia, 44.46±29.08 in Parkinson's disease and 43.02 in Alzheimer's disease. A test of significance between groups showed significant differences between postsubarachnoid hemorrhage NPH and control groups, postsubarachnoid hemorrhage NPH and vascular dementia groups, and postsubarachnoid hemorrhage NPH and Parkinson's disease groups (p<0.005, p<0.0001, p<0.005). No significant difference was found between control group and vascular dementia or Parkinson's disease group (FIG. 1).

Example 2

Determination of L-PGDS Levels in the Cerebrospinal Fluid of Control Subjects and Patients with Presenile NPH and Senile NPH and Dementia L-PGDS levels in the CSF collected from the lumbar vertebra of controls (8 cases) and patients with presenile NPH (under 70 years of age: 7 cases), senile NPH (at or more than 70 years of age: 8 cases), dementia excluding NPH (a total of 7 cases including 4 cases of cerebrovascular dementia, 1 case of Parkinson's disease, 2 cases of Alzheimer's disease) were determined.

Figure 2:
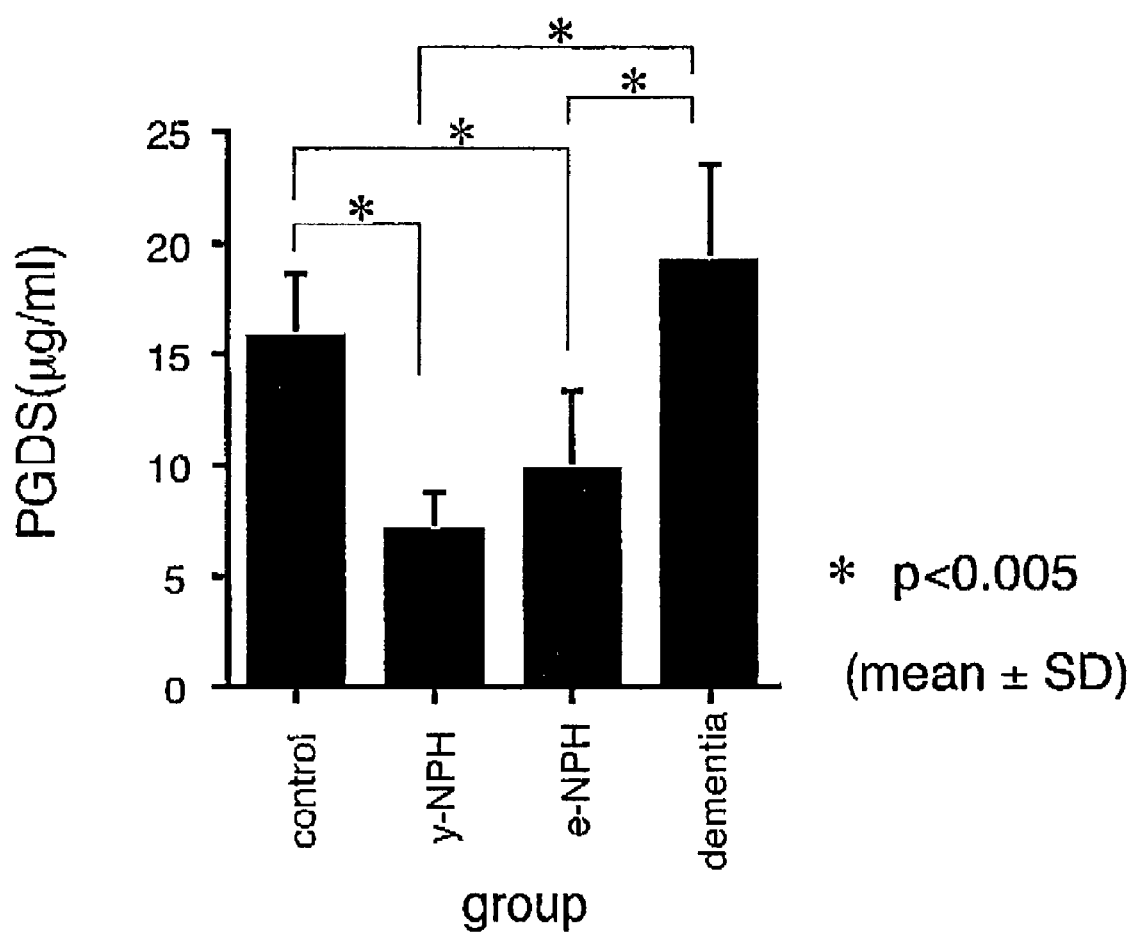
FIG. 2 shows assay results of L-PGDS levels in the cerebrospinal fluid of controls and patients with presenile NPH (y-NPH) and senile NPH (e-NPH) and dementia.

As a result, L-PGDS levels in the CSF of each group were 15.70±2.97 (μg/ml, mean±SD) in control group, 7.05±1.69 in presenile NPH group, 10.04±3.73 in senile NPH group and 19.14±4.34 in dementia group. As shown in FIG. 2, L-PGDS levels in the cerebrospinal fluid of both presenile NPH and senile NPH groups were significantly lower as compared with both control and dementia groups (p<0.005). (In the figure, y-NPH means presenile NPH, e-NPH means senile NPH and dementia means dementia excluding NPH).

Example 3

Determination of Neuron Specific Enolase (NSE) and S-100 Protein Levels in the Cerebrospinal Fluid of Control Subjects and Patients with Presenile NPH and Senile NPH and Dementia CSF samples collected from individuals of each group were centrifuged (1500 g, 10 minutes) to give 0.5 ml of cell-free supernatants, which were stored at −20° C. and assayed for neuron specific enolase (NSE) and S-100 protein levels indicative of brain parenchymal damage. NSE was determined by radioimmunoassay using an NSE assay kit (Eiken, Tokyo, Japan) and S-100 protein was determined with S-100 immunoradiometric assay kit (Sangtec Medical, Sweden).

Figure 3:
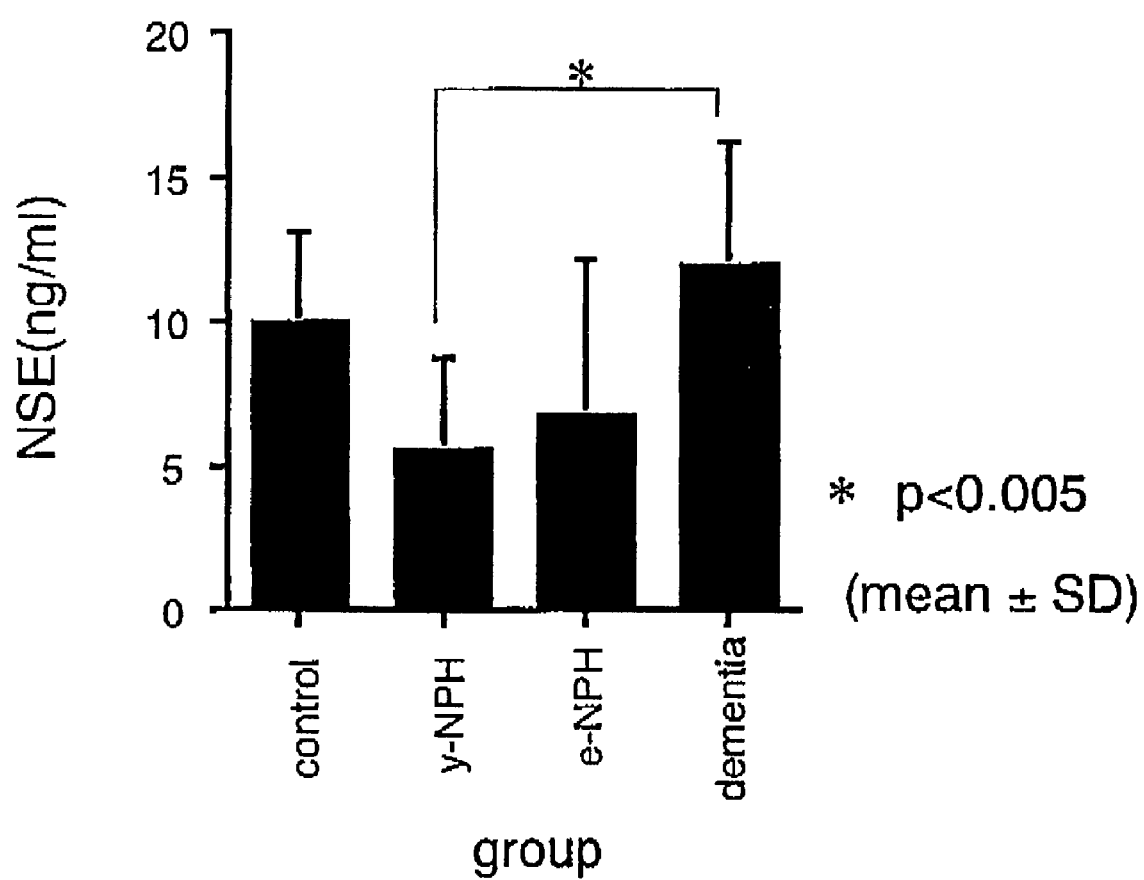
FIG. 3 shows assay results of neuron specific enolase (NSE) levels in the cerebrospinal fluid of control subjects and in patients with presenile NPH (y-NPH) and senile NPH (e-NPH) and dementia.
Figure 4:
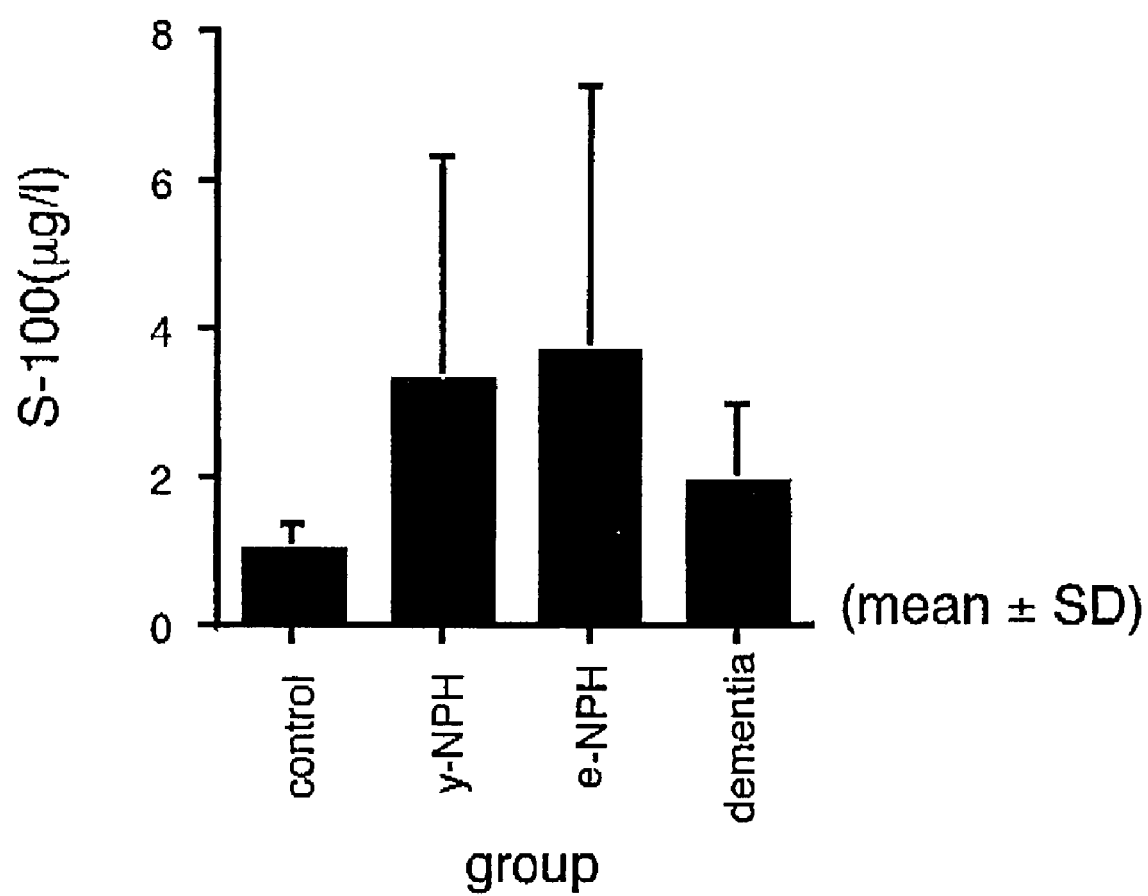
FIG. 4 shows assay results of S-100 protein levels in the cerebrospinal fluid of controls and patients with presenile NPH (y-NPH) and senile NPH (e-NPH) and dementia.

As a result, NSE levels in the CSF of each group were 9.90±3.19 (ng/ml, mean±SD) in control group, 6.13±3.01 in presenile NPH group, 7.37±5.42 in senile NPH group and 11.86±4.38 in dementia group (FIG. 3). On the other hand, S-100 protein levels were 0.98±0.38 (μg/ml, mean±SD) in control group, 3.27±3.04 in presenile NPH group, 3.68±3.61 in senile NPH group and 1.94±1.06 in dementia group (FIG. 4). NSE levels in cerebrospinal fluid showed no significant difference between groups except that presenile NPH group showed significantly lower levels than dementia group. S-100 protein levels in cerebrospinal fluid showed no significant difference between groups.

The foregoing results showed that NPH, which could not be detected by other indicators, can be detected and differentiated from other demential diseases by determining L-PGDS levels in CSF in comparison with normal levels.

The invention claimed is:

1. A method to facilitate diagnosis of normal pressure hydrocephalus (NPH), comprising:
    measuring the concentration of human lipocalin-type prostaglandin D synthase (L-PGDS) in a test sample of cerebrospinal fluid collected from a test subject, and
    comparing the concentration of the human L-PGDS in the test sample with normal levels of human L-PGDS, said normal levels being determined from control subjects not suffering from NPH,
    wherein a significantly lower concentration of human L-PGDS in said test sample taken from the test subject, compared to normal levels of human L-PGDS is an indication that the test subject has NPH.

2. The method of claim 1, wherein the normal pressure hydrocephalus is symptomatic normal pressure hydrocephalus or idiopathic normal pressure hydrocephalus.

3. The method of claim 1 or 2, wherein the concentration of human lipocalin-type prostaglandin D synthase is measured by an immunoassay.

4. The method of claim 3, wherein the concentration of human lipocalin-type prostaglandin D synthase is measured by sandwich ELISA using a monoclonal antibody specific to human lipocalin-type prostaglandin D synthase.

* * * * *